(12) United States Patent
Pianca et al.

(10) Patent No.: US 7,953,497 B1
(45) Date of Patent: May 31, 2011

(54) INSERTION STYLET

(75) Inventors: Anne M Pianca, Valencia, CA (US);
Michael S Colvin, Malibu, CA (US);
David K. L Peterson, Saugus, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 476 days.

(21) Appl. No.: 10/635,091

(22) Filed: Aug. 6, 2003

Related U.S. Application Data

(60) Provisional application No. 60/401,279, filed on Aug. 6, 2002, provisional application No. 60/401,280, filed on Aug. 6, 2002.

(51) Int. Cl.
*A61N 1/372* (2006.01)

(52) U.S. Cl. .................................. 607/117; 604/170.02

(58) Field of Classification Search .................. 600/378; 604/170.02, 164.01; 607/117
See application file for complete search history.

(56) References Cited

U.S. PATENT DOCUMENTS

| | | | |
|---|---|---|---|
| 3,646,940 A | 3/1972 | Timm et al. | |
| 3,724,467 A | 4/1973 | Avery et al. | |
| 3,822,708 A | 7/1974 | Zilber | |
| 4,253,462 A | 3/1981 | Dutcher et al. | |
| 4,498,482 A | 2/1985 | Williams | |
| 4,545,390 A * | 10/1985 | Leary | 600/462 |
| 5,069,226 A * | 12/1991 | Yamauchi et al. | 600/585 |
| 5,098,411 A | 3/1992 | Watson et al. | |
| 5,163,912 A | 11/1992 | Gay et al. | |
| 5,217,026 A * | 6/1993 | Stoy et al. | 600/585 |
| 5,238,004 A | 8/1993 | Sahatjian et al. | |
| 5,357,961 A * | 10/1994 | Fields et al. | 600/435 |
| 5,522,875 A | 6/1996 | Gates et al. | |
| 5,722,425 A | 3/1998 | Bostrom | |
| 5,728,148 A | 3/1998 | Bostrom et al. | |
| 5,807,339 A | 9/1998 | Bostrom et al. | |
| 5,916,178 A * | 6/1999 | Noone et al. | 600/585 |
| 5,957,966 A | 9/1999 | Schroeppel et al. | |
| 6,059,771 A | 5/2000 | Balbierz et al. | |
| 6,165,140 A * | 12/2000 | Ferrera | 600/585 |
| 6,168,571 B1 | 1/2001 | Solar et al. | |
| 6,214,016 B1 | 4/2001 | Williams et al. | |
| 6,270,496 B1 | 8/2001 | Bowe et al. | |
| 6,607,496 B1 * | 8/2003 | Poor et al. | 600/585 |
| 6,755,794 B2 * | 6/2004 | Soukup | 600/585 |
| 7,074,197 B2 * | 7/2006 | Reynolds et al. | 600/585 |

* cited by examiner

*Primary Examiner* — Michael Kahelin
(74) *Attorney, Agent, or Firm* — Frommer Lawrence & Haug LLP; Patrick R. Turner

(57) ABSTRACT

A stylet is provided which has improved stiffness and buckling strength and can be easily manufactured at low cost. The stylet is comprised of a covering and a core, each of which have different mechanical properties. In one embodiment, the stylet is comprised of an outer tube and an inner rod with a circular cross-section, wherein the rod is inserted inside the tube. The tube can be made from a material which is more resistant to permanent deformation than the inner rod. The inner rod is made from a stiffer material which provides buckling strength. The combination of the stylet and associated stimulation lead may be used to make multiple insertions into body tissue.

11 Claims, 4 Drawing Sheets

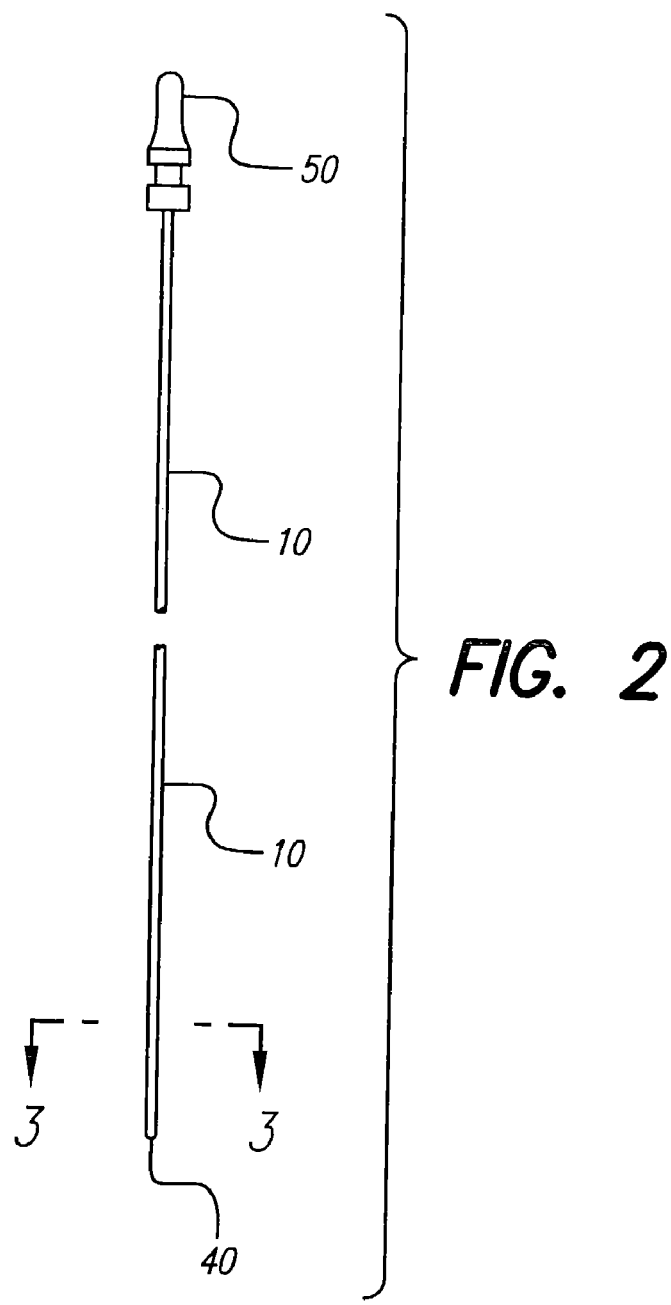
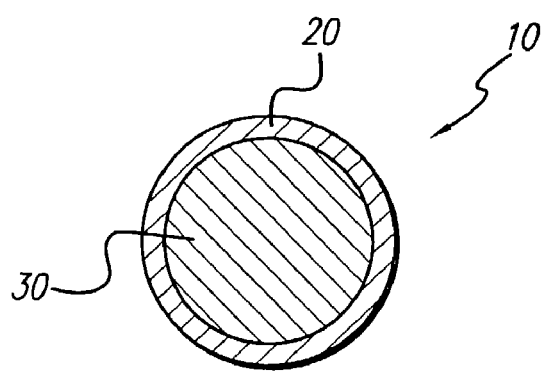

INSERTION STYLET

The present application claims the benefit of U.S. Provisional Patent Application Ser. No. 60/401,279, filed 6 Aug. 2002, and Provisional Patent Application Ser. No. 60/401,280, filed 6 Aug. 2002, which applications are herein incorporated by reference.

BACKGROUND OF THE INVENTION

The present invention relates to medical lead systems and, more particularly, to insertion stylets used with medical stimulating leads.

The term "stylet," as used in this disclosure, is an implement inserted into the lumen of a stimulating lead to stiffen the lead and to facilitate its insertion into a target tissue. The term "rod," in one form of use, is an implement that is placed inside a cannula to provide support to the cannula while it is inserted into target tissue. The term "rod," in another form of use, describes an elongate object.

The term "lead," as used herein, will refer to an elongate conductor covered by insulation and which conductor is connected to an electrode contact. An "electrode contact" is a conductive material that is exposed to the tissue to be stimulated. An "electrode", on the other hand, generally refers to that part of the lead that includes the electrode contact as well as a portion of insulation or other lead structure near the electrode contact. The term "electrode" may be used, herein, interchangeably with a stimulating lead. The term "tract" refers to an individual pathway formed in tissue, e.g., the brain, by inserting a microelectrode, a macroelectrode, a lead or an associated cannula into that tissue.

The term "microelectrode" refers to a recording electrode, for instance, used in deep brain stimulation (DBS), which microelectrode can be essentially an insulated conducting wire that has at least the distal portion of the wire uninsulated to receive electrical signals from the recorded tissue. The term "macroelectrode" will refer to a DBS temporary stimulating electrode having an electrode contact and parts connected to the electrode contact, which macroelectrode is intended as a temporary test electrode to perform macrostimulation. Macrostimulation involves stimulating many brain cells at once.

Deep brain stimulation is being increasingly accepted as a viable treatment modality. In particular DBS applied to the thalamus for treatment of tremor was approved by the FDA in 1997. Subsequently, other diseases, such as Parkinson's disease, dystonia and chronic pain, among others, have been identified as candidates for treatment with deep brain stimulation.

Implantation of a lead for deep brain stimulation generally involves the following preliminary steps: (a) anatomical mapping and (b) physiological mapping. Anatomical mapping involves mapping segments of an individual's brain anatomy using non-invasive imaging techniques, such as magnetic resonance imaging (MRI) and computed axial tomography (CAT) scans. Physiological mapping involves localizing the brain site to be stimulated. Step (b) can be further divided into: (i) preliminarily identifying a promising brain site by recording individual cell activity with a microelectrode and (ii) confirming physiological stimulation efficacy of that site by performing a test stimulation with a macroelectrode.

Microelectrode recording is generally performed with a small diameter electrode with a relatively small surface area optimal for recording cell activity. The microelectrode may be essentially a wire which has at least the distal portion uninsulated to receive electrical signals. The microelectrode functions as a probe to locate a promising brain site. Since a number of attempts may be required to locate the precise target site, it is desirable that the microelectrode be as small as possible to minimize trauma when the microelectrode is placed into the brain, in some cases, multiple times.

Once a brain site has been identified, a macroelectrode is used to test whether the delivered stimulation has the intended therapeutic effect. A macroelectrode is a temporary stimulating electrode which is not intended to be chronically implanted. Because macrostimulation involves stimulating many cells at once, an optimal electrode for macrostimulation requires a larger contact surface area compared to a microelectrode, which merely records electrical activity from a single cell or a few cells. For this reason, the electrode contact surface of a macroelectrode is generally larger than the electrode contact surface of a microelectrode. After a promising brain site has been identified with microelectrode cell recordings, the macroelectrode can be retraced through the same pathway to the same brain site.

Test stimulation with the temporary macroelectrode may need to be performed in a number of tracts in order to localize the site which provides the proper physiological effect. Because the macroelectrode may need to be repeatedly inserted into the brain, the macroelectrode must be durable, stiff and resistant to buckling. As the macroelectrode is intended for repeated use, it is made from a sterilizable material.

After macrostimulation has confirmed that stimulation at the brain site provides the intended physiological effect, the macroelectrode is withdrawn from the brain and a DBS lead is permanently implanted at the exact site.

Keeping in mind the above general steps, a conventional procedure for carrying out DBS may involve the following detailed steps: (1) place a stereotactic frame on the subject, which stereotactic frame is a device temporarily mounted on the head to assist in guiding the lead system into the brain; (2) perform MRI or equivalent imaging of the subject with the stereotactic frame; (3) identify a theoretical target using a planning software; (4) place the subject with the stereotactic frame in a head rest; (5) using scalp clips, cut the subject's skin flap in the head, exposing the working surface area of the cranium; (6) place the stereotactic arc with target coordinate settings and identify the location on skull for creation of a burr hole; (7) remove the arc and drill a burr hole in the patient's skull; (8) place the base of the lead anchor; and (9) with the microelectrode recording drive attached, and with an appropriate stereotactic frame adaptor inserted into the instrument guide, place the stereotactic arc.

Next, (10) advance a microelectrode cannula and an insertion rod into the brain until they are approximately 25 mm above the target; (11) remove the insertion rod, leaving the cannula in place; (12) insert a recording microelectrode such that the tip of the microelectrode is flush with the tip of the microelectrode cannula; (13) connect the connector pin of the recording microelectrode to a microelectrode recording system; (14) starting approximately 25 mm above the target, advance the microelectrode into a recording tract at the specified rate using the microdrive; and (15) if the target is identified, proceed to step 16. If the target is not identified, proceed with the following: (17) using the recording results and pre-operative imaging, (a) determine a new set of coordinates for the theoretical target; (b) disconnect the recording microelectrode from the microelectrode recording system; (c) remove the recording microelectrode cannula and recording microelectrode; and (d) adjust the coordinates of the stereotactic frame. Then, continue at step 10, above.

Next, (16) remove the recording microelectrode cannula and recording microelectrode; (17) insert a macroelectrode insertion cannula and rod until they are approximately 25 mm above the target; (18) remove the insertion rod, leaving the macroelectrode insertion cannula in place; (19) insert a stimulating macroelectrode, and advance it to the target stimulation site identified by the recording microelectrode; (20) using macrostimulation, simulate the stimulation of the chronic DBS lead to ensure proper physiological response; (21) remove the macroelectrode and cannula; (22) insert a DBS lead insertion cannula and an insertion rod, and advance both to approximately 25 mm above the stimulation site; (23) remove the insertion rod; (24) insert a DBS lead, with stylet, through the insertion cannula, and advance the lead/stylet to the stimulation site; (25) electrically connect the lead to a trial stimulator; and (26) perform the desired stimulation and measurements using any one or combination of four electrodes on the DBS lead.

Next, (27) if the results are favorable, proceed to step 28. If the results are not favorable, proceed with the following: (a) using the macrostimulation results, and microelectrode recording results, as well as pre-operative imaging, determine a new set of coordinates for the theoretical target; (b) remove the lead and stylet; (c) remove the insertion cannula; (d) adjust the coordinates of the stereotactic frame; and (e) continue at step 10, above.

Next, (28) remove the stylet, followed by the insertion cannula; (29) using macrostimulation, verify that micro-dislodgement of the DBS lead has not occurred; and, finally, (30) lock the DBS lead in the lead anchor. Some physicians might use additional steps, fewer steps, or perform the steps in a different order.

The above-described surgical procedure is far from ideal. There are many steps which lengthen the surgical procedure and increase surgical risk. For example, retracing the microelectrode or macroelectrode pathway increases the chance for misalignment and misplacement. In particular, misalignment may occur in retracing the location of the microelectrode with the macroelectrode and, further, in retracing the location of the macroelectrode with the permanent DBS lead. Retracing problems arise because separate cannulas must be placed each time into the brain to introduce the microelectrode, the macroelectrode and the permanent DBS lead. The use of three, separate cannulas significantly heightens the chance of mistracing and adds additional steps to the lead implant procedure. Mistracing can add surgical time because the procedure must be performed over and because expensive stimulating leads are likely to be scrapped. In addition, more procedural steps not only increases surgical time, but also increases the risk of peri-operative complications and the chance for post-operative infections.

In addition to DBS, another common medical application that uses a stylet in concert with a stimulating lead is spinal cord stimulation (SCS). Spinal cord stimulation is a well-accepted clinical method for reducing chronic, intractable pain. A spinal cord stimulation system typically includes an implanted pulse generator (IPG) and a stimulating lead, which lead is comprised of lead conductor wires and electrode contacts that are connected thereto. The IPG generates electrical pulses that are delivered to the dorsal column nerves within the spinal cord through the electrode contacts which are implanted along the dura of the spinal cord. In a typical situation, the attached leads exit the spinal cord and are tunneled around the torso of the patient to a subcutaneous pocket where the pulse generator is implanted. Representative SCS systems and leads are disclosed in the following patents: U.S. Pat. Nos. 3,646,940; 3,724,467; and 3,822,708.

Spinal cord stimulation requires a lead/stylet combination that has a very high resistance to kinks and high buckling strength since the lead/stylet combination is pushed through muscle, fascia and other tissue. The lead should preferably have a small diameter profile to facilitate ease of insertion into tissue. Because the lead has a small diameter, the stylet, by necessity, must also have a small diameter profile in order to fit inside the lead lumen. At the same time, the lead/stylet should preferably offer mechanical characteristics which enable multiple insertions into tissue, without breaking or permanently bending.

Conventional stylets and guidewires for the SCS application are typically made of stainless steel or tungsten. Tungsten is a malleable, linear elastic material. A stylet made from tungsten is flexible and does not easily break but, unfortunately, has poor kink resistance. "Kink resistance" will be used, hereinafter, as a term to describe the ability of the wire to be bent into a relatively tight bend radius without incurring permanent deformation. Once a stylet kinks, the stylet/lead combination may have to be withdrawn from the tissue because the permanent bend in the stylet makes it difficult to steer the lead/stylet combination within the tissue. The ability to steer the lead is critical for achieving optimal stimulation in spinal cord stimulation where a positional difference of a few millimeters may mean the difference between poor or effective stimulation. If the stylet kinks during use, both the stylet and lead may need to be scrapped because the bent stylet cannot be easily extracted from the lead without causing further damage to the lead or dislodging the lead from the tissue site.

Super-elastic materials provide excellent kink resistance but have poor resistance to buckling forces and torquing and so a stylet made from this material alone would not be suitable for use with a spinal cord stimulation lead. Stylets and guidewires manufactured from combinations of linear and super-elastic materials have been evaluated, as disclosed in U.S. Pat. Nos. 6,214,016; 6,168,571; 5,238,004; 6,270,496 and 5,957,966. A guidewire, for example, is taught in U.S. Pat. No. 6,214,016. This guidewire, however, is very complicated to assemble and use and has a relatively large diameter.

Accordingly, there is a need to have a stylet or guidewire that has a very small diameter and exhibits mechanical properties ideal for SCS or DBS application, including high buckling strength and resistance to kinking, yet is relatively inexpensive and easy to manufacture. Such an improved stylet would allow multiple insertions of the lead/stylet into tissue and reduce the scrapping of leads and stylets. For the DBS application, there is a further need to reduce the number of surgical steps in order to reduce surgical time and operative risk and to improve the accuracy of placing the permanent DBS lead.

SUMMARY OF THE INVENTION

The present invention addresses the above and other needs by providing a stylet having sufficient stiffness, flexibility and resistance to buckling.

In accordance with an aspect of the invention, there is provided a stylet comprising an exterior (outer) covering and an inner core, wherein the mechanical characteristics of the exterior (outer) covering and the core are different and contribute to a stylet having improved mechanical characteristics for use with a medical stimulation lead intended to be inserted into body tissue, e.g., the brain.

In one embodiment of the stylet, the covering is in the form of an outer tube and the inner core is in the form of a preformed rod inserted into the tube. For example, the tube may have mechanical characteristics which make it more resistant to kinking, while the inner rod may be comparatively stiffer and more resistant to buckling forces. In a further embodiment, the pre-formed rod may be pre-stressed to allow it to operate on the compression side of the stress-strain curve. Alternatively, it is possible to reverse the types of materials used such that the covering is more resistant to buckling and the core is a super-elastic material.

In one embodiment, the stylet, along its length, may have a substantially constant (isodiametric) outer diameter but the wall thickness of the outer covering may vary along the stylet length. The core would also vary in diameter along the length of the stylet but in a manner which compensates for the variable wall thickness of the covering, but still yielding an isodiametric stylet.

In yet another embodiment, the stylet may have a variable diameter or thickness along the length of the stylet. The covering, along the stylet length, may have a variable thickness and the core diameter may be substantially constant or may also be variable. Alternatively, the covering may have a constant thickness along the stylet length and the core may have a variable diameter or thickness.

In another aspect of the present invention, a medical lead system is provided comprising a stylet and stimulating lead, wherein the stylet has an outer covering and inner core, the outer covering and inner core having different mechanical characteristics and, wherein the stylet and stimulating lead can be used together in combination to make multiple insertions into tissue without breaking or becoming permanently deformed.

It is thus a feature of the present invention to provide a stylet which has the composite properties of kink resistance and resistance to buckling, as well as mechanical flexibility to permit the stylet to be easily inserted into a lead lumen, withdrawn from the lead and re-inserted into the same or different stimulating lead as the circumstances warrant.

It is another feature of the present invention to provide a stylet which can be used in combination with a stimulation lead which combination may be inserted into multiple insertion tracts.

Specifically for the DBS application, the stylet, in combination with a DBS stimulating lead, may function as a macroelectrode and the same DBS lead may be implanted chronically, thereby eliminating the use of a separate, temporary macroelectrode.

It is yet a further feature of the present invention to provide a stylet that can be easily manufactured at relatively low cost. In addition, costs can be reduced because the stylet or the stylet/lead combination can be reused for multiple tracts and, hence, fewer leads and stylets will be scrapped.

Thus, the present invention provides an improved stylet which can be used advantageously in DBS and SCS applications, among other stimulation applications.

BRIEF DESCRIPTION OF THE DRAWINGS

The above and other aspects, features and advantages of the present invention will be more apparent from the following more particular description thereof, presented in conjunction with the following drawings wherein:

FIG. 2 shows, in accordance with the present invention, a view of the stylet alone without a stimulating lead;

FIG. 3 shows, in accordance with the present invention, a cross-sectional view of the stylet of FIG. 2 at line 3-3 showing the outer covering and core;

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The present invention provides, in one aspect, an improved stylet that may be used in various applications such as deep brain stimulation (DBS) and spinal cord stimulation (SCS). It will be appreciated by those skilled in the art that the stylet of the present invention is not limited to DBS and SCS applications but may be used for other applications that utilize stylets, such as, for example, cardiac stimulation.

The stylet of the present invention comprises an outer covering and a core, each part made from different materials contributing different mechanical properties. For example, the outer covering can be a kink resistant, relatively flexible material which does not have high buckling strength, whereas the inner core material can be comparatively more stiff and resistant to buckling forces, although more brittle than the outer covering. In one embodiment of stylet, the outer covering can be in the form of a tube and the inner core may be in the form of a pre-formed rod that is inserted into the tube. In yet a further embodiment of the stylet, the pre-formed rod may be pre-stressed to permit the rod to operate on the compression side of the stress-strain curve.

Figure 1:
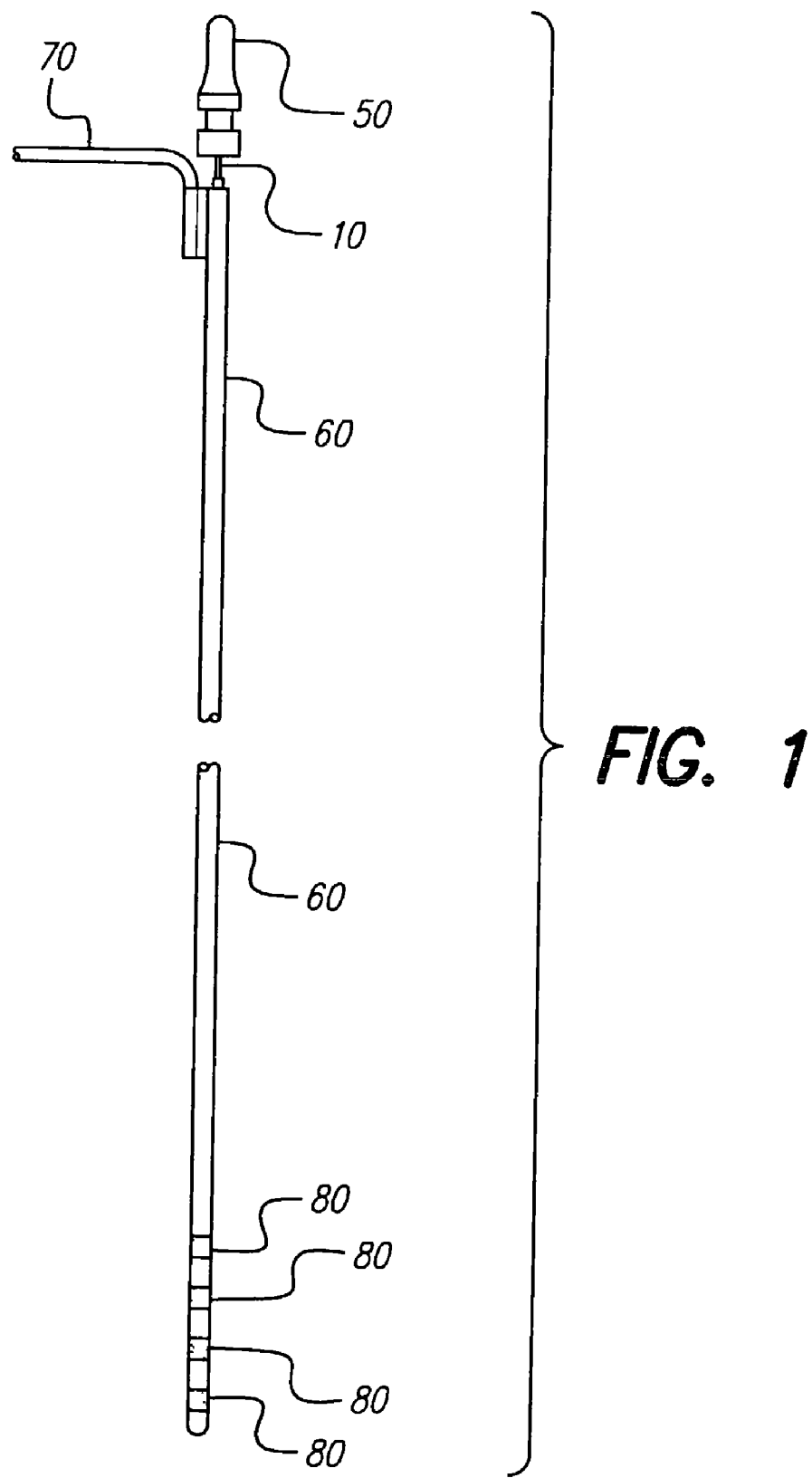
FIG. 1 shows, in accordance with the present invention, the system comprising the improved stylet inserted into a lead lumen, this combination having mechanical characteristics to enable multiple insertion into tissue.

FIG. 1 shows a view of the stylet 10 of the present invention inserted into the lumen of a conventional stimulation lead 60. The stimulation lead 60 has a bend 70 at the proximal end to direct the conductor wires connecting the electrode contacts 80 away from the lead 60 and to permit insertion of the stylet 10 into the lead. The stimulation lead 60 has, at its distal end, four electrode contacts 80. An electrode array having about four electrode contacts is a preferred configuration for the DBS application. A larger number of electrode contacts, for example between eight to sixteen, are preferred in the SCS application. The stylet 10 can have a handle 50 which can be used to help insert the stylet 10 into the lead 60 and also help facilitate the insertion of the stylet/lead combination through body tissue.

FIG. 2 shows, in accordance with the present invention, a view of the stylet 10 only. The stylet 10 has a distal tip 40 which can be rounded on the end. This separate tip may be welded, glued or attached by other means to the stylet 10.

FIG. 3 shows a cross-sectional view of the stylet 10, as shown in FIG. 2 along line 3-3, which stylet has an outer covering 20, in this case, in the form of a tubing, and an inner material or core 30. The inner material may be either a filling material or a pre-formed rod that is inserted into the tubing lumen. The pre-formed rod may be pre-stressed to permit it to operate on the compression side of the stress-strain curve. The outer tubing 20 may be made of a relatively flexible material which is not subject to fracturing or permanent deformation.

Figure 4:
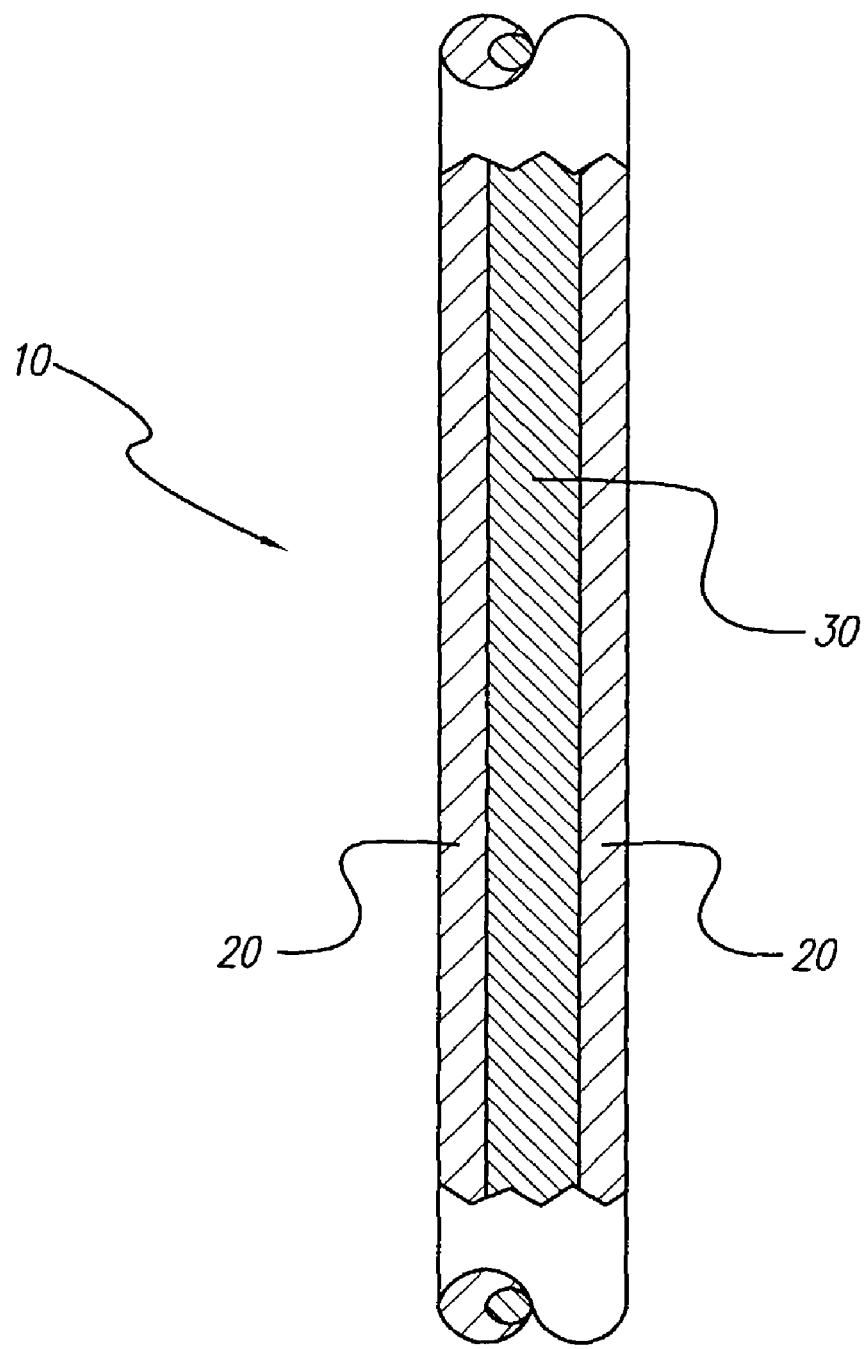
FIG. 4 shows, in accordance with the present invention, a cross-sectional, cut-away view of a portion of the stylet depicted in FIG. 2, which cut-away shows the stylet's outer covering and core.

FIG. 4 shows a cut-away, longitudinal, cross-sectional view of a segment of the stylet of FIGS. 2 and 3. In this view, the outer covering 20 is in the form of a round tube and the inner core 30 is a pre-formed rod inserted into the tube. Alternatively, a filling material may be used as the core 30, which material hardens inside the tube.

Figure 5:
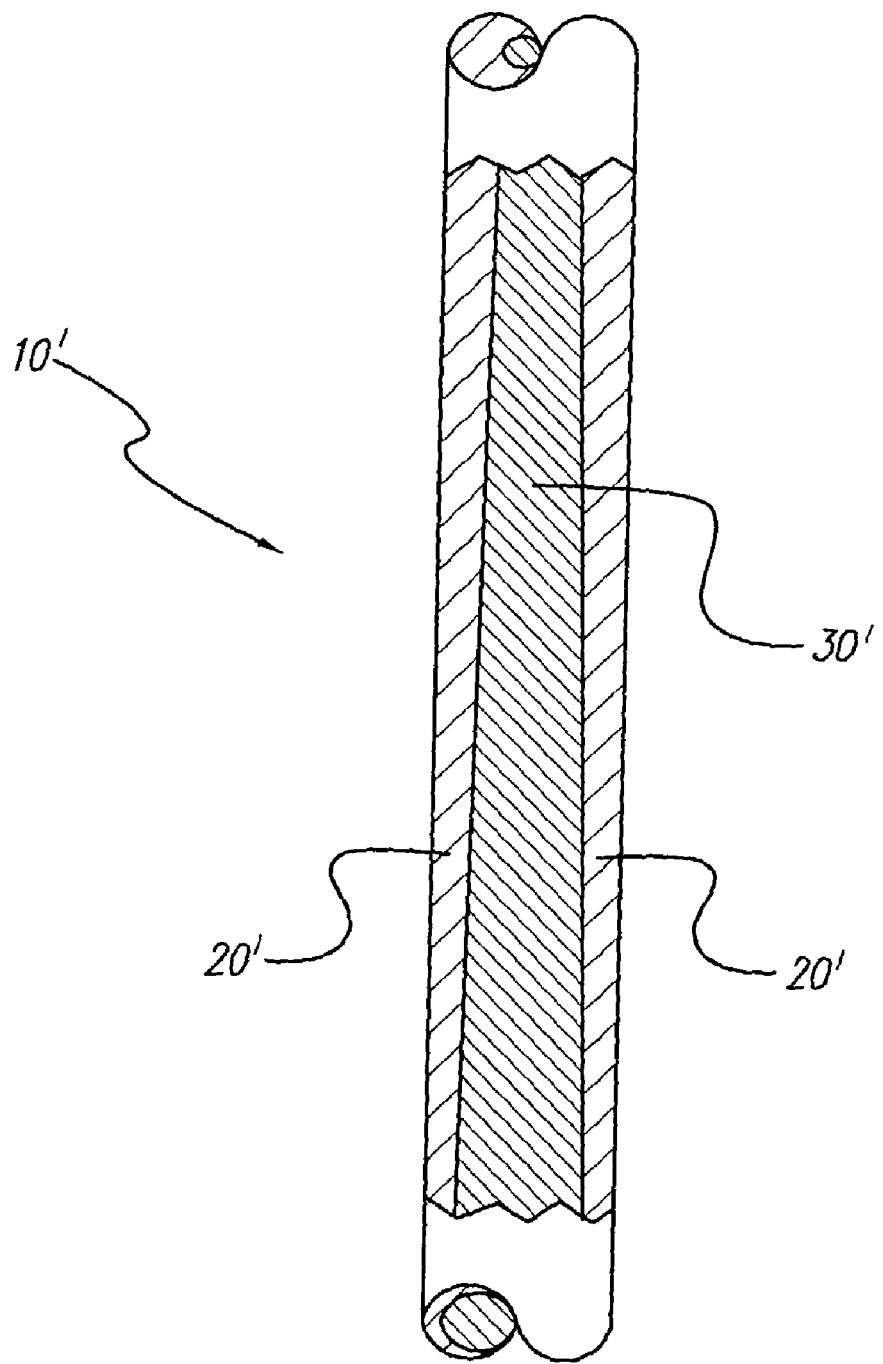
FIG. 5 shows, in accordance with the present invention, an alternative embodiment showing a cross-sectional, cut-away view of a portion of the stylet depicted in FIG. 2.

FIG. 5 shows yet another embodiment of the stylet 10', in accordance with the present invention, wherein the core 30' diameter or thickness varies along the length of the stylet 10', while the outer circumference along the length of the stylet remains isodiametrically constant. As shown in FIG. 5, both the core 30' and outer covering 20' vary in thickness along the length of the stylet 10'. Moreover, the outer covering at the distal end of the stylet (bottom of FIG. 1) may be thinner than the proximal end of the stylet (top of FIG. 1).

Other embodiments of the stylet, in accordance with the present invention, can have an outer covering that has a variable thickness along the stylet length, whereas the core diameter or thickness remains the same along the stylet length. Alternatively, the core diameter or thickness may vary and the thickness of the outer covering may be substantially constant along the length of the stylet. As a further alternative, both the covering and core may vary in their thicknesses along the length of the stylet. If desired, the stylet can also be pre-formed with a radius or bend that can be introduced during manufacture.

The cross-section of the outer tubing 20 may be chosen from a number of shapes, among them, a square, rectangle, triangle or a circle (annulus). Calculations of critical buckling load for the various shaped tubular cross-sections indicate that a circular (annular) cross section achieves the highest buckling load relative to the maximum cross-sectional width of the outer tubing. While the cross-sectional shape of the outer tubing may be chosen to be any number of shapes, a preferred shape is a circular (annular) cross-section.

One particular embodiment of the stylet, in accordance with the present invention, can be used with an SCS lead. The outer covering which is in the form of a tubing 20 (or 20') can be made of a super-elastic material which is resistant to breaking and kinking. A preferred material for the tubing 20 is 425 nitinol which is an alloy of 50% nickel and 50% titanium. Depending on the application, other nitinol alloys having different percentages of nickel and titanium may be used. When the tubing 20 is 425 nitinol, the material for the core 30, which is a pre-formed rod, is preferably 316 stainless steel. 316 stainless steel is comparatively stiffer than nitinol. The pre-formed rod may also be made of tungsten and platinum. An exemplary SCS stylet can have a nitinol tube with an outer diameter of about 0.0102" and inner diameter of about 0.0067". The rod 30 can be 316 stainless steel with an outer diameter of about 0.004".

During manufacturing of the SCS stylet, the nitinol tube can be cast or drawn through hardened steel dies to the desired circumferential shape. The pre-formed core (rod) can be molded, machined or extruded to the proper shape and diameter. In one method of manufacturing the stylet, the core is made slightly smaller in diameter than the inner diameter of the outer tube. With the core placed inside the tube, the nitinol tube can be drawn over the core by pulling the tube through a die. The drawn assembly is heated to a temperature above 400° C. for several minutes to set the nitinol over the core. Then, the assembly is quickly quenched or, alternatively, is rapidly air cooled. The resulting composite stylet can withstand high torque and high buckling forces during use. These specific mechanical properties are obtained because the super-elastic outer covering of nitinol provides greater kink resistance and the pre-formed rod, made of 316 stainless steel, contributes greater resistance to buckling forces.

Alternatively, as another embodiment of the SCS stylet, in accordance with present invention, the type of materials may be reversed; the core may be a super-elastic material, while the outer covering is a stiffer material that is resistant to buckling forces.

With respect to DBS surgery, the continuing objectives are: reduce surgical duration; reduce the risk of post-operative infections by eliminating unnecessary procedural steps; increase the accuracy of lead placement; and reduce the need to scrap DBS stylets and leads due to incorrect placement.

As performed in conventional surgical DBS implant procedures, separate steps are required for inserting the microelectrode, the macroelectrode and the permanent DBS lead into the brain. In particular, the microelectrode is optimized for individual cell recording and use as a probe because its small size minimizes bleeding and trauma. The temporary macroelectrode, having a comparatively larger electrode surface area, is optimized to deliver current to stimulate hundreds or thousands of cells. The DBS stimulating lead also functions to stimulate many cells like the macroelectrode. But unlike the macroelectrode, the DBS lead has mechanical characteristics which are optimized for chronic, permanent implantation. As such, the conventional DBS lead is flexible because it is designed to be chronically implantable. This flexibility, however, defeats the insertion of the conventional DBS lead into multiple tracts because it cannot withstand the repeated buckling forces experienced during insertion. A macroelectrode, in contrast, can be made mechanically stiffer, resistant to higher buckling loads, and can be used repeatedly in multiple tracts. The macroelectrode does not need to be flexible, because it is not intended to be implanted chronically.

A representative conventional stylet for use with a DBS lead is provided by Medtronic, Inc. (not shown). This stylet is made from a solid, 0.014" tungsten wire which has a higher yield strength than many stainless steels (such as cold drawn 304). In choosing a stylet which is either malleable or brittle, the safer choice is generally a malleable stylet to avoid the possibility of breaking during insertion of the lead into tissue. While a malleable stylet presents the disadvantage that it may bend during insertion, and thus makes performing multiple tracts impossible, on the other hand, a thin, brittle stylet presents the disadvantage that it may break in use.

A DBS stimulation lead may be made from one or more strands of wound conductor coil. This winding may be accomplished in a manner to provide an axial lumen running through the stimulation lead. At the distal end of the lead, the conductor coil can be connected to one or more electrode contacts and, at the proximal end of the lead, the conductor coil can be connected to an electrical connector. The electrode contacts interface with brain tissue and can deliver a current to cause the brain cells to be stimulated. In general, the extreme thinness of the DBS lead causes it to be flexible and deformable during implantation. Thus, to temporarily increase the DBS lead stiffness during implantation, a DBS stylet is typically inserted inside the lead's axial lumen.

The fragility of the DBS lead, in combination with a conventional bendable tungsten stylet, prevents the combination from being inserted into multiple tracts in the brain. If a tract proves unsuccessful, at least the stylet must be withdrawn and discarded because it typically becomes permanently bent after one use. Sometimes the DBS lead also becomes permanently bent. A separate macroelectrode, not being designed for chronic placement (where some lead flexibility may be desired) but merely for temporary testing, however, can be designed to be more stiff, robust and resistant to buckling and, hence, such a temporary macroelectrode can be reused many times.

Given that insertion and withdrawal of separate cannulas for the macroelectrode and the permanent lead lengthens surgical duration and increases risk of infection, it would be particularly desirable if the permanent DBS lead could perform the macrostimulation confirmation step with multiple tracts and, in addition, be chronically implantable.

In accordance with another aspect of the present invention, a lead system comprising a stylet and stimulating lead may be used particularly for deep brain stimulation which permits the DBS stimulating lead to be used as a macroelectrode and also to be chronically implanted as a DBS lead. Furthermore, the stylet can be made, in accordance with the invention, to exhibit mechanical properties such that a DBS lead/stylet combination may be used to conduct macrostimulation and to probe multiple tracts in the brain.

Referring again to FIG. 1, the stylet and stimulating lead system shown is one which may be used for the DBS application. The stylet 10 is inserted into the lumen of DBS lead 60. The DBS lead 60 has a lumen through the axial length of the lead in which the stylet 10 is inserted therethrough. The DBS lead preferably has more than one electrode contact 80 and in this particular example is quadripolar, i.e., has four electrode contacts 80. The bend 70 at the proximal end of the lead 60 can contain at least N number of connecting conductors that connect to N number of electrode contacts 80. This bend can be helpful in DBS applications to direct conducting wires transversely from the lead's axial direction. A handle 50 is placed proximally on the stylet, which handle can facilitate inserting the stylet into the DBS lead 60, as well as inserting the combined DBS lead/stylet into the brain.

For the DBS application, some examples of outer tubing materials that may be used include: 304 stainless steel, 316 and 316L stainless steel, and nitinol (425 nickel-titanium alloy). The inner material 30 should be comparatively stiffer than the outer tubing material. Some examples of the inner material which may be used include: ceramic, epoxy, hard polyurethane, magnesia partially stabilized Zirconia and Yttria partially stabilized Zirconia.

The stylet and DBS lead system of the present invention eliminates the use of a separate macroelectrode. For the DBS application, the stylet should have an outer, flexible tubing (which is not necessarily super-elastic, as with the SCS stylet) and have a comparatively stiff and, to some degree, a brittle, inner rod. Such a DBS stylet provides high buckling strength while resisting permanent deformation when used with a DBS stimulating lead. These mechanical characteristics allows the stylet to be used in conjunction with a stimulating lead to replace the function of a separate, macroelectrode. The stylet/DBS lead system of the present invention therefore can be advantageously inserted into the brain multiple times for performing macrostimulation in multiple tracts without breaking or kinking.

Because no separate macroelectrode is needed, the stylet/DBS lead system of the present invention eliminates the risk of inserting an additional cannula, thereby saving a step and reducing operative risk. Additionally, once an ideal brain site is located with stylet/DBS lead, which functions as a macroelectrode, the stylet can be withdrawn and the DBS lead can be left in place. Misalignment problems are eliminated because an additional (macroelectrode) cannula does not need to be inserted and retraced over the path of the cannula used to place the microelectrode. In the conventional lead placement procedure, if such misalignment occurs during retracing, an additional step may be required to re-locate the target site and, therefore, increase surgical duration. Furthermore, the use of the stylet of the present invention can shorten surgery time since the stylet/DBS lead can be inserted together to perform multiple tracts. In summary, using the stylet/DBS lead combination of the present invention can reduce the scrapping of stylets and DBS leads, increase the accuracy of lead placement and reduce the risks of surgery.

Thus, the improved stylet design presents a number of advantages over the currently known stylets and guidewires. First, the stylet may be manufactured to have composite mechanical properties according to the combined mechanical characteristics of the covering and core. The stylet can be made to have the desired properties of improved kink resistance, high flexibility and resistance to high buckling forces. Second, the stylet can be made inexpensively and easily since the materials that may be selected are readily available at a reasonable cost.

While the invention herein disclosed has been described by means of specific embodiments and applications thereof, numerous modifications and variations could be made thereto by those skilled in the art without departing from the scope of the invention set forth in the claims.

What is claimed is:

1. A stylet for use with a medical stimulating lead, the stylet comprising:
    an elongated body having a proximal end, a distal end, a length, and an outer diameter along the length, wherein the outer diameter of the body is isodiametric;
    a handle disposed at the proximal end of the body, wherein the handle has an outer diameter that is larger than the outer diameter of the body; and
    a rounded tip glued or welded directly to the distal end of the body;
    wherein the body comprises an outer covering that is a tube, the outer covering made of a metal outer covering material and having an inner diameter and a solid annular lateral cross-section;
    wherein the body also comprises a solid inner core made of inner core material, the inner core being disposed inside the outer covering and having an outer diameter and a solid lateral cross-section;
    wherein the outer covering material and inner core material have different elastic and buckling properties;
    wherein the inner diameter of the outer covering and the outer diameter of the inner core vary along the length of the body such that the inner diameter of the outer covering decreases distally along the length of the body and the outer diameter of the inner core increases distally along the length of the body, while the outer diameter of the lead remains isodiametric.

2. The stylet of claim 1, wherein the outer covering material is a super-elastic material, which outer covering material is substantially more resistant to permanent bending deformation than the inner core material; and wherein the inner core material is a linear elastic material, which inner core material is substantially more resistant to buckling than the outer covering material.

3. The stylet of claim 2, wherein the inner core material is selected from the group consisting of cold drawn 304 stainless steel, 316 stainless steel, and 316L stainless steel; and wherein the outer material is nitinol (425 nickel-titanium alloy).

4. The stylet of claim 3, wherein the inner core is a preformed rod.

5. The stylet of claim 1, wherein the inner core material is a super-elastic material, which inner core material is substantially more resistant to permanent bending deformation than the outer covering material; and wherein the outer covering material is a linear-elastic material, which outer covering material is substantially more resistant to buckling than the inner core material.

6. The stylet of claim 5, wherein the outer covering material is selected from the group consisting of cold drawn 304 stainless steel, 316 stainless steel, and 316L stainless steel; and wherein the inner core material is nitinol (425 nickel-titanium alloy).

7. The stylet of claim 1, wherein the outer covering defines a tube and the inner core is a pre-formed rod that has been pre-stressed so that the inner core operates on the compression side of the stress-strain curve.

8. The stylet of claim 1, wherein the stylet has a solid lateral cross-section along the length of the body.

9. The stylet of claim 1, wherein the stylet is pre-formed with a bend.

10. The stylet of claim 2, wherein the inner core material is formed from tungsten and platinum.

11. The stylet of claim 1, wherein the inner core material comprises at least one of ceramic, epoxy, magnesia partially stabilized zirconia, or yttria partially stabilized zirconia.

* * * * *